United States Patent [19]

Stewart

[11] Patent Number: 4,829,987

[45] Date of Patent: May 16, 1989

[54] MINERAL BODY WRAP COMBINED WITH EXERCISE FOR TREATING CELLULITE

[75] Inventor: Roger D. Stewart, Sioux Falls, S. Dak.

[73] Assignee: Easy Tone Body Systems, Inc., Sioux Falls, S. Dak.

[21] Appl. No.: 940,340

[22] Filed: Dec. 11, 1986

[51] Int. Cl.⁴ .................. A61H 1/00; A61H 36/00
[52] U.S. Cl. .................... 128/65; 604/890.1; 272/93
[58] Field of Search .............. 272/93; 128/402, 65; 604/897

[56] References Cited

U.S. PATENT DOCUMENTS

| | | | |
|---|---|---|---|
| 1,305,439 | 6/1919 | Brennan | 128/402 |
| 1,604,435 | 10/1926 | Wharton | 128/65 |
| 3,970,078 | 7/1976 | Rogers, Jr. | 128/57 |
| 4,086,922 | 5/1978 | Henderson | 128/24.3 |
| 4,525,359 | 6/1985 | Greenway, III et al. | 514/258 |
| 4,588,724 | 5/1986 | Greenway, III et al. | 514/321 |

OTHER PUBLICATIONS

"Trim-Eze", Sweat Suit, Marcy Catalog, Marcy Gymnasium Equipment Company, Glendale, Calif., Oct. 7, 1969, p. 42.
M. J. Saffon's Body Lift, by M. J. Saffon, Warner Books, Inc. Warner Publication Co., Jan. 1984.
Brochure of California Concept, 4-1986.
Brochure of Slender You, Inc., 1986.
Brochure of Table Toners, Inc.

Primary Examiner—Edgar S. Burr
Assistant Examiner—Tonya Lamb
Attorney, Agent, or Firm—Merchant, Gould, Smith, Edell, Welter and Schmidt

[57] ABSTRACT

The present invention relates to a method for treating the human body to reduce body dimensions and minimize the undesirable appearance of cellulite. The method includes combining a mineral solution with body wrap material, then wrapping this material on the body portion to be treated, and then passively exercising that body portion.

1 Claim, 2 Drawing Sheets

MINERAL BODY WRAP COMBINED WITH EXERCISE FOR TREATING CELLULITE

TECHNICAL FIELD OF THE INVENTION

The present invention pertains generally to the field of medicine, and more particularly to the field of cellulite removal from the human body.

BACKGROUND OF THE INVENTION

Cellulite is a layman's term for the medical condition which causes the skin and soft colloidal tissues of the body to appear lumpy and pitted. Cellulite is caused by toxified fatty deposits in the normal fat cells of the body. It occurs almost exclusively in women. It is believed to result from the monthly hormonal changes and normally high estrogen levels found in women. In time, the toxicity gradually atrophies the surface of the muscle base supporting the deposits, causing pitting. In addition, the toxicity inhibits the function of elasticin in the colloidal tissues, a substance which functions to "tighten" the soft tissues of the body. The weakened and softened colloidal tissues covering the muscle base thus accentuate every bump, dip, and bulge, resulting in the telltale appearance known as cellulite.

Cellulite is quite unsightly, and is, therefore, the cause of considerable embarrassment and shame among those who suffer from it. Accordingly, there is a strong demand for cellulite reducing treatments.

SUMMARY OF THE INVENTION

The present invention provides a method for reducing cellulite in the human body. According to the method of the invention, there is provided a mineral solution for extracting certain minerals from fatty deposits in the human body. The body areas to be treated are wrapped with elastic bandages soaked in said mineral solution. An exercise machine having a static table portion and a reciprocating portion for moving a selected portion of the patient's body is provided, and the patient lays on the static table portion of the machine so that said selected portion of the body is moved in a reciprocating manner by the reciprocating portion of the machine. To exercise, the patient resists the motion in order to exercise one or more muscle groups. Preferably, the exercise is carried out for a predetermined period of eight to ten minutes per unit, after which the bandages are removed and the patient washed to remove mineral solution residue.

BRIEF DESCRIPTION OF THE DRAWINGS

In The Drawings:

FIG. 1 illustrates the thigh-exercising machine;
FIG. 2 shows the buttock-exercising machine;
FIG. 3 illustrates the stomach-toning machine;
FIG. 4 shows the upper body exercising machine;
FIG. 5 shows the hip-toning machine;
FIG. 6 shows the waist-exercise machine; each suitable for use in carrying out the method of the present invention; and FIG. 7 illustrates a human body in which a body portion is wrapped in accordance with the present invention.

DETAILED DESCRIPTION OF THE INVENTION

The present invention combines a mineral solution body wrap and conditioning with dynamic isometric exercise equipment to extract certain minerals from fatty deposits and thereby revitalizing the elastin of the soft body tissue. The result is a significant reduction in cellulite and significant improvement in the cosmetic appearance of the treated areas. The effects of the combined wrap and exercise program can last up to a year or more if the client's wrap weight is maintained.

The method of the present invention involves wrapping the patient to be treated and subjecting the patient to one or more special dynamic isometric exercise machines. Preferably, the present invention employs a proprietary body wrap commercially available from European Body Wrap, Inc., 40 Glenn Caravan Circle, Sparks, Nev. 89431. Other mineral solutions that may be used in the present invention are disclosed in the book entitled M. J. Saffon's Body Lift, M. J. Saffon, Warner Books Inc., Warner Publication Company, printed January 1984, the entire disclosure of which is hereby incorporated herein by reference. In particular, the mineral solutions disclosed in this book on pages 93, 97, 98 and 107 are believed to be suitable for the purposes of the present invention.

Figure 7:
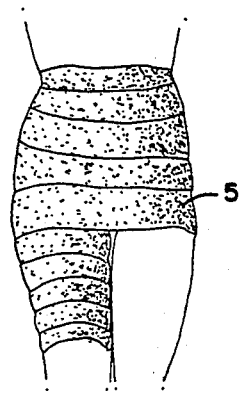
FIG. 7 illustrates the application of mineral-soaked bandages to the body.

Preferably, as shown in FIG. 7, the wrap is done using six inch wide elastic bandage type wraps 5 that are soaked in the proprietary mineral solution, which as best known consists of an all natural sea clay mud solution. The wrap acts like a giant poultice which extracts certain minerals and electrolytes from the body tissue. The areas most affected by cellulite are the thighs, hips, abdomen and bust area, and these areas at least are preferably wrapped for each treatment; although if desired virtually the entire body can be wrapped from ankle to neck and jaw line. Although it is preferable that the wrap be applied directly to bare tissue, it may be applied over some fabrics, most notably cotton, which do not interfere with the action of the solution.

Preferably, two 18 quart ovens are provided to warm the mineral solution and to warm the bandages prior to applying them to the client. After the wraps have been warmed to approximately 150° F., they are dipped in the warm mineral solution (also kept at approximately 150° F.), and then wrapped on the patient's body. Preferably, the mineral solution is initially brought to a boil to sterilize it. Once the wrap has been completed, the patient is helped into a vinyl exercise suit and put through a series of dynamic isometric exercise machines. The exercise suit is preferably vinyl to prevent evaporation and to aid in getting the skin pores to open up to allow the poultice effect of the mineral solution to work better. Also, the suit is loose fitting. Exercise is important because it increases metabolism and circulation in the affected areas and thereby the interaction of the mineral wrap with the body tissue, allowing the tissue to more readily release its fluids and minerals to the wrap and to the waste extracting components of the circulatory system. The exercise also tends to firm up the muscle tissue underlying the treated areas to provide a smoother supporting substrate.

Referring now to FIGS. 1-6 there will be shown the dynamic isometric exercise machines used in the treatment method of the present invention. These machines are manufactured by Sun Industries, Inc. of Jonesboro, Ark., and are commercially available through the Fredric's Corporation, 4235 Mulhauser Rd., Fairfield, Ohio 45014 and Great Tan, Inc. 3100 West 12th Street, Sioux Falls, S.D. 57104. Generally each machine calls for the patient to exercise selected muscle groups in isolation and with relatively little body movement. The unexercised body portions can remain essentially unexerted. Each machine has a moving portion, thus the term "dynamic," which actually provides the force for moving the exercised body portion. Exercise of the selected muscle groups is effected by resisting the motion of the machine in a manner similar to the techniques used in isometric exercise.

Figure 1:
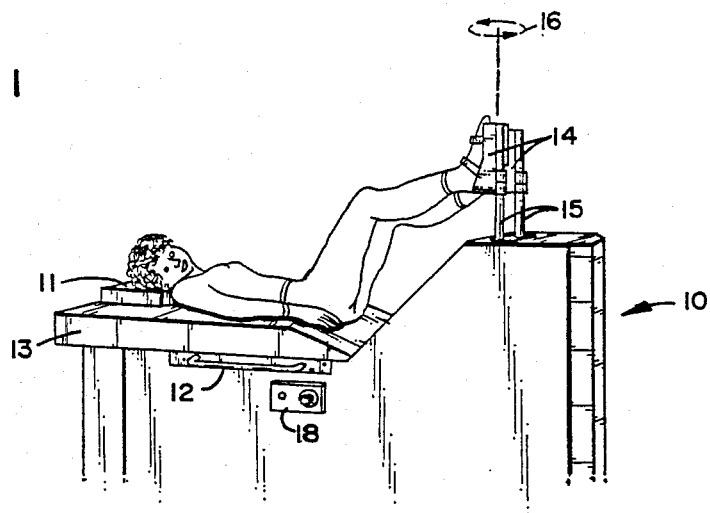
FIGS. 1-6 illustrate various dynamic isometric exercise machines used in the method of the present invention.

FIG. 1 shows the thigh-exercising machine 10. To use the machine, a patient lays on her back with her head on the square pillow 11 and hips near the edge of the pad 13. There are handles 12 on the sides to hold if the patient needs them for leverage while pulling with the legs. The patient's feet are strapped in the footrests 14, with the heels on the edge of the footrests. The feet are rolled to their sides so that the patient's knees are dropped outwardly. When the machine is activated via controls 18, the footrests 14 go around in a circular motion about the axes of their verticle supports 15 in the pattern indicated by arrow 16. To tone the inner thigh, the patient attempts to pull the footrests back toward herself using the entire leg area as the footrests move outward and away. This machine exercises the whole leg area. It reduces the calves and the fat pads around knees. It tones and firms the upper thigh area, concentrating on the inner thigh, and also tones the hips.

To tone the outer thighs, the knees should be even with the footrest and not out past them. The hips should be back further from the edge than in the inner thigh position. As the footrests move inward and toward the patient, the patient pulls back toward themselves with the knees together and drop out to side. The exercise is effective for reducing "saddlebags."

To exercise the back of the thigh, the hips should be in the middle of curved area of pad 13 and the knees locked together. This emphasizes exercise of the calf and back of the thigh area.

Figure 2:
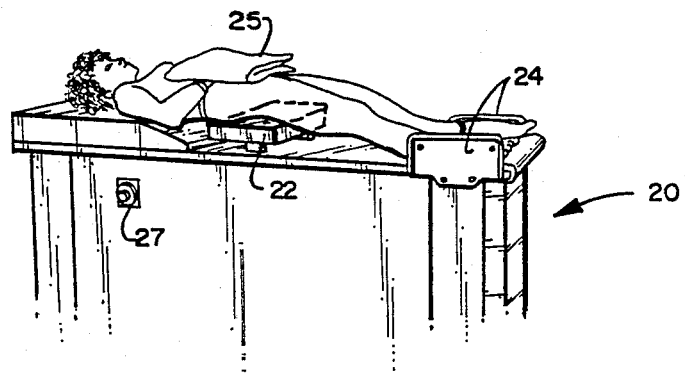

FIG. 2 shows the buttock exercising machine 20. The patient lays on the back with the head at the top of the table, feet apart, touching the sides 24. The waistline is even with the top of the small pad 22. Without arching the back, the patient stretches up in the ribcage. The hands are folded flat, placed at the lowest part of the ribcage and holding in and up. A ten pound sandbag 25 is placed on the stomach. When the machine is activated via control 27, pad 22 rocks back and forth, working against the weight of the respective buttocks. Pad 22 rocks from the position shown to a height of about 1 to 1½ inches above the table. The patient holds in the stomach and buttock muscles as long as they can, then relax, and try it again when able. This table exercises the stomach and hips also. It firms and tones muscles, hips and buttock, actually helping to lift the buttock. The extra 10 pounds of weight applied to the stomach helps the patient use the stomach muscles and also applies pressure so that the table works better on the hips. This exercise is especially helpful in ridding the body of cellulite by increasing the circulation in and massaging the buttock area.

Figure 3:
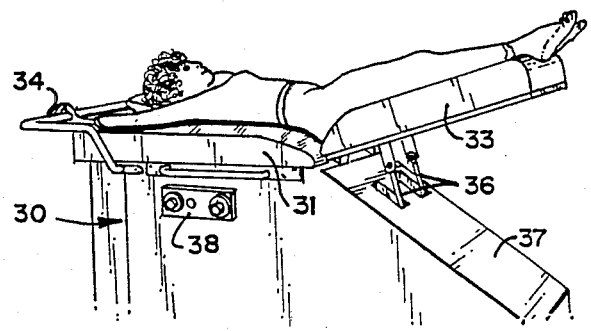

FIG. 3 shows, the stomach toning machine 30. The patient lays on the back, in the center of the table, with the head at the top of the table and the feet together. The buttocks is above the separation of the two cushions 31 and 33. Lying flat, the patient reaches the hands above the head; underneath bar 34. Preferably, the bar is adjustable so it can be held comfortably, while feeling a stretch through the stomach and ribcage. The stomach is held in while the machine is on. The top section of the machine which supports cushion 31 is stationary, with the cushion 33 being moved up and down with linkages 36. The cushion 33 moves between the illustrated position and a down position approximately parallel to surface 37 to achieve about 28 inches of movement. Preferably, the patient tries to move the legs with the pad to get better results. Control 38 also includes a speed adjustment to regulate the frequency of repetitions. This machine strengthens and tightens muscles in the midriff, abdomen and waist; reducing inches in these area. Muscles in the lower back area are strengthened and stretched also; increasing overall flexibility.

Figure 4:
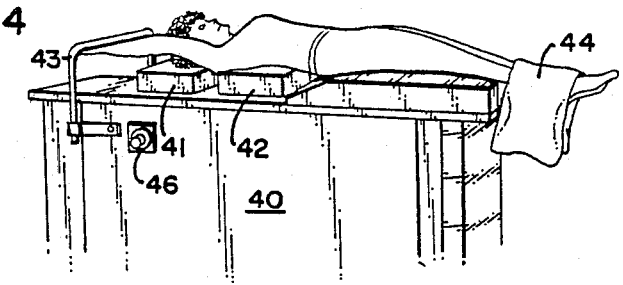

The upper-body exercising machine 40 is shown in FIG. 4. The patient lays on the back with the head on pad 41, with top of the shoulders even with the top of the second pad 42. The feet are kept together and the stomach is held in tight. The arms are stretched back toward the stationary bar 43, the hands under the bar and the arms in close to the ears. The bar is used as a guide, and the palms are bounced against the bar with each movement of the machine. When activated via control 46, pad 42 rocks back and forth; the pad 42 rocks about 1 to 1½ inches up at the maximum. The patient stretches back as far as possible, as if reaching for something back toward the front of the table. The neck is kept relaxed. A ten pound sandbag 44 goes across the ankles. The feet are preferably flexed with the toes pointing upwardly. This machine exercises the entire upper part of the body. It lifts the ribcage, tones and lifts the bustline, improves posture, tones, firms and reduces the upper back, upper arms, waistline, midriff and stomach. It also helps reduce the fat pad between the shoulder blades.

Figure 5:
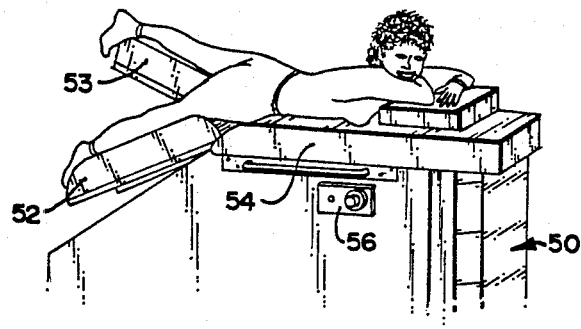

The hip-toning machine 50 is shown in FIG. 5. The top of the patient's legs are positioned even with the top of the two kick pads 52 and 53, preferably the legs are positioned out to the sides of the kick pads and body relaxed. When activated via control 56, pads 52 and 53 move up and down about 24 inches in an alternating fashion, hinged on their interior ends near where they meet pad 54. While operating, the patient concentrates on keeping the legs on the kick pads as they lift them, with the legs out to the sides and the body relaxed. The stomach muscles are preferably held in. The patient should remain stationary.

Figure 6:
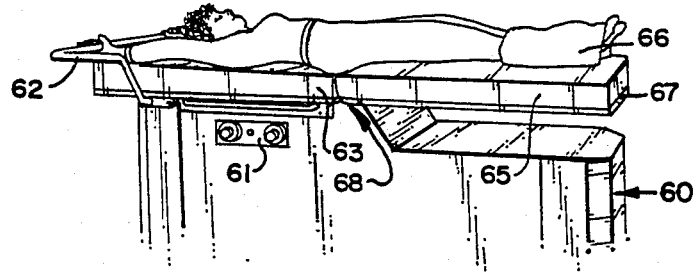

The waist exercise machine 60 is shown in FIG. 6. To use the machine the patient lays on her back in the center of table, with the head at the top of the table toward the bar 62, and the feet together. The waistline is kept even where cushions 63 and 65 meet. Lying flat, the patient reaches her hands above her head, underneath the bar 62, to cause a stretch through the stomach and ribcage. A ten pound sandbag 66 is placed on the feet to keep them in place. When the machine is activated via control 61, legs support platform 67 moves from side to side through an approximate 30 to 35 degrees arc, pivoting about the interior end 68 of support platform 67. Preferably, the patient keeps the body muscles tight, especially the stomach muscles. This machine preferably includes a speed adjustment to allow adjustment to individual needs.

For the sake of brevity in the drawing, the interior mechanisms of machines 10, 20, 30, 40, 50 and 60 have not been illustrated. It shall be understood, however, that any number of different mechanical linkages can be employed to move the moving parts of each machine throughout their respective motions, as would be readily apparent to those skilled in the relevant arts.

Thus, as described above, machines 10-60 provide a dynamic form of isometric exercise which reduces the fatigue and strain normally associated with traditional exercise regimens such as weight lifting or aerobics. The machines are less strenuous than weight lifting programs and calisthenics, and exercise virtually all the muscles in the body, thus toning the muscles and tendons. All the machines effectively assist in the strengthening of muscles and help improve body flexibility with little or no risk of injury.

Preferably, the patient spends eight to ten minutes on each machine. To aid in timing each session, each of the machine controls preferably includes a timing mechanism which may be set to time an eight minute session and then shut the machine off. Preferably, each patient engages in approximately sixty to seventy minutes of exercise total using the above-described machines and performing a few other bending, stretching and twisting exercises, such as toe touches and trunk twists. Afterward, the wrap is removed and the patient dresses.

Every movement and exercise done against the tight wrap is extremely toning intensive, because every movement and exercise done has a total resistance from the wrap. In addition, since the body is wrapped in an extremely supportive manner and due to the controlled nature of the exercise, many arthritics, low back sufferers and others may benefit from the present invention where other forms of "free exercise" would be prohibited. The present invention develops a firmer, smoother, muscle base, and firms, tones and compacts the overlying tissue.

Thus, as may be readily appreciated, the present invention provides an ideal combination of body wrap and exercise program. The machines are particularly effective for exercising while wrapped because the resistance of the wrap is partially overcome by the motive forces provided by the machine. This allows the patient to flex muscles that might otherwise be difficult to flex against the resistance of the wrap. Also, the machines provide a safe, controlled and low-key exercise discipline for those with physical limitations, allowing each individual to exert against the machine according to her own ability. Accordingly, little aerobic capacity is required; this allows the treatment to be extended to the obese who might other treatment wise be unable to engage in sufficient exercise to facilitate the full effect of the mineral wrap.

Although the invention has been described above in its preferred form, those skilled in the art will appreciate that various modifications, additions and changes may be made thereto without departing from the spirit and scope of the claims appended hereto. For instance, it is contemplated that other dynamic isometric exercise machine configurations could be devised to accomplish the exercise results achieved with machines 10-60, or to exercise other muscle groups not specifically addressed by machines 10-60. Also, it is contemplated that other mineral wraps that extract unwanted cellulite exist and may be substituted for the above-identified preferred wrap.

I claim:

1. A method for treating a human body containing cellulite, said method comprising:
   (a) applying a mineral solution to body wrapping material, said mineral solution being of a type suitable for reducing cellulite disfigurement in the human body;
   (b) wrapping the human body area to be treated with said wrapping material containing mineral solution;
   (c) passively exercising said wrapped body area while the human body is lying on an exercise machine having a static table portion and a reciprocating portion for moving a selected portion of the wrapped body area;
   (d) moving said reciprocating portion while the selected portion of said wrapped body area is resisting said movement thereby exercising said wrapped body area; and
   (e) removing said wrapping material from the body area and washing the residue of said mineral solution from the body area.

* * * * *